US009149298B2

United States Patent
Freudiger

(10) Patent No.: US 9,149,298 B2
(45) Date of Patent: Oct. 6, 2015

(54) ANCHORAGE ARRANGEMENT FOR A CONNECTING ROD FOR THE STABILIZATION OF THE SPINE

(75) Inventor: Stefan Freudiger, Bremgarten b. Bern (CH)

(73) Assignee: SPINESAVE AG (CH)

( * ) Notice: Subject to any disclaimer, the term of this patent is extended or adjusted under 35 U.S.C. 154(b) by 103 days.

(21) Appl. No.: 13/382,976

(22) PCT Filed: Jul. 1, 2010

(86) PCT No.: PCT/CH2010/000168
§ 371 (c)(1),
(2), (4) Date: Jan. 9, 2012

(87) PCT Pub. No.: WO2011/006267
PCT Pub. Date: Jan. 20, 2011

(65) Prior Publication Data
US 2012/0123480 A1    May 17, 2012

(30) Foreign Application Priority Data

Jul. 16, 2009  (CH) ...................................... 1113/09

(51) Int. Cl.
*A61B 17/70*    (2006.01)
(52) U.S. Cl.
CPC ............ *A61B 17/701* (2013.01); *A61B 17/7031* (2013.01); *A61B 17/7032* (2013.01)
(58) Field of Classification Search
CPC ........................... A61B 17/70–17/7013; A61B 17/7019–17/7031
USPC ......... 606/246, 254–255, 258–259, 261–262, 606/264–278
See application file for complete search history.

(56) References Cited

U.S. PATENT DOCUMENTS

| | | | |
|---|---|---|---|
| 6,440,132 B1* | 8/2002 | Jackson | 606/308 |
| 7,125,410 B2* | 10/2006 | Freudiger | 606/254 |
| 7,597,707 B2* | 10/2009 | Freudiger | 606/254 |
| 2004/0260284 A1* | 12/2004 | Parker | 606/61 |
| 2005/0203518 A1* | 9/2005 | Biedermann et al. | 606/61 |
| 2005/0240180 A1* | 10/2005 | Vienney et al. | 606/61 |
| 2006/0025768 A1* | 2/2006 | Iott et al. | 606/61 |
| 2006/0241594 A1* | 10/2006 | McCarthy et al. | 606/61 |
| 2007/0093820 A1* | 4/2007 | Freudiger | 606/61 |
| 2007/0270843 A1* | 11/2007 | Matthis et al. | 606/61 |

(Continued)

FOREIGN PATENT DOCUMENTS

| | | |
|---|---|---|
| EP | 1364622 B1 | 7/2005 |
| EP | 1527742 B1 | 7/2006 |

(Continued)

OTHER PUBLICATIONS

Notification Concerning Transmittal of International Preliminary Report on Patentability (Chapter 1 of the Patent Cooperation Treaty) dated Jan. 26, 2012 issued in corresponding International Application No. PCT/CH2010/000168 (6 pages).

(Continued)

*Primary Examiner* — Eduardo C Robert
*Assistant Examiner* — Michelle C Eckman
(74) *Attorney, Agent, or Firm* — Ostrolenk Faber LLP

(57) ABSTRACT

Plastic rod anchorage for the surgical treatment of the spine where the plastic rod (1) has at least two plane-parallel surfaces (1a) in order to uniformly clamp the rod (1) on its entire circumference.

15 Claims, 6 Drawing Sheets

(56) References Cited

U.S. PATENT DOCUMENTS

| | | | |
|---|---|---|---|
| 2007/0293862 A1* | 12/2007 | Jackson | 606/61 |
| 2008/0086130 A1* | 4/2008 | Lake et al. | 606/61 |
| 2008/0086132 A1* | 4/2008 | Biedermann et al. | 606/61 |
| 2008/0177318 A1* | 7/2008 | Veldman et al. | 606/256 |
| 2008/0183216 A1* | 7/2008 | Jackson | 606/278 |
| 2008/0262556 A1* | 10/2008 | Jacofsky et al. | 606/308 |
| 2009/0048632 A1* | 2/2009 | Firkins et al. | 606/246 |
| 2009/0138052 A1* | 5/2009 | Biedermann et al. | 606/301 |
| 2009/0163955 A1* | 6/2009 | Moumene et al. | 606/257 |
| 2009/0254128 A1* | 10/2009 | Zehnder et al. | 606/302 |
| 2010/0063544 A1* | 3/2010 | Butler | 606/261 |
| 2010/0106193 A1* | 4/2010 | Barry | 606/264 |
| 2011/0238116 A1* | 9/2011 | Takemoto | 606/261 |
| 2011/0270313 A1* | 11/2011 | Justis et al. | 606/261 |

FOREIGN PATENT DOCUMENTS

| | | |
|---|---|---|
| EP | 1759646 B1 | 7/2008 |
| FR | 2829014 A1 | 3/2003 |

OTHER PUBLICATIONS

International Search Report dated Sep. 10, 2010, issued in corresponding international application No. PCT/CH2010/000168.

Office Action dated Dec. 28, 2011 issued in corresponding European Application No. 10 731 707.5-1526 (6 pages).

* cited by examiner

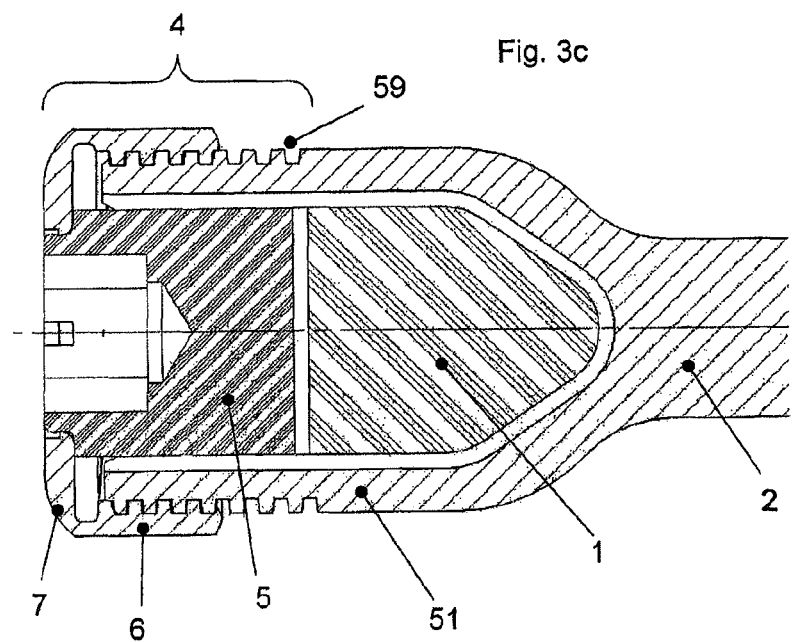

ANCHORAGE ARRANGEMENT FOR A CONNECTING ROD FOR THE STABILIZATION OF THE SPINE

CROSS REFERENCE TO RELATED APPLICATIONS

The present application is a 35 U.S.C. §371 National Phase conversion of PCT/CH2010/000168, filed Jul. 1, 2010, which claims benefit of Swiss Application No. 1113/09, filed Jul. 16, 2009, the disclosure of which is incorporated herein by reference. The PCT International Application was published in the English language.

FIELD OF THE INVENTION

The present invention relates to an anchorage arrangement for a connecting rod for stabilizing a spine.

BACKGROUND OF THE INVENTION

For stabilizing the spine, pedicle screws are inserted in the spine and their heads are interconnected by a rod. In order to maintain a dynamic behavior, elastic rods are known as an alternative to rigid metallic rods.

Since elastic rods are often manufactured from plastic materials, and plastic materials are generally susceptible to creep, plastic rods cannot simply be clamped by a press-fit as this is easily possible, for example, with metal rods.

Therefore, for a reliable long-term clamping of plastic rods (i.e. made of polymeric material), particular devices are required.

Only few methods to this end are known in the art so far. These will be explained below and their disadvantages as compared to the present invention will be pointed out.

The inventions according to patent specifications EP 1 364 622 B1 (Freudiger) and EP 1 527 742 B1 (Freudiger) show positive or form-fit anchorages. The rod and its seat in the screw head are provided with geometrically mutually fitting grooves. However, positioning the grooved surfaces requires precise introduction to avoid canting. Furthermore, grooved surfaces do not allow continuous positioning.

The invention according to patent specification EP 1 759 646 B1 (Freudiger) shows a frictional anchorage with an indirect form-fit. The connecting rod is smooth and is clamped between two members, the screw head and a laterally guided spacer, whose contour nominally deviates from the rod contour in the area of contact. Therefore, this nominal contour deviation locally penetrates into the rod such that high stress intensities result in the clamped areas and relative movements due to shear deformation in the non-clamped areas. Furthermore, rod material may flow off between the clamping areas if they do not form a closed cage.

SUMMARY OF THE INVENTION

Accordingly, it is an object of the present invention to propose an anchorage arrangement for a connecting rod exerting less stress on the rod while maintaining positioning accuracy.

Such an anchorage arrangement includes the connecting plastic rod including at least two plane-parallel surfaces; and one or more bone screws, each bone screw including sidewalls defining an opening positioned and configured to receive the connecting plastic rod; and a clamping device comprising a clamping element and a spacer together positioned and configured to provide a clamping action in a direction parallel to the at least two plane-parallel surfaces so as to clamp an entire circumference of the rod, such that a distance between the sidewalls is adapted to a distance of the plane-parallel surfaces in an area of contact so that the rod is snugly slideable in the opening. The invention will be further explained by means of preferred exemplary embodiments with reference to the Figures. They show schematically:

BRIEF DESCRIPTION OF THE DRAWINGS

FIG. 3c The rod in the mounted condition in the variant having an external nut and a separate spacer.

DESCRIPTION OF PREFERRED EMBODIMENTS

A plastic rod 1 is anchored in a pedicle screw 2 such that it can be introduced in a continuous manner without creating stress peaks in the anchoring area due to local clamping as a result of deviating contours and without any alteration of the rod cross-section by flowing of the material. Furthermore, the anchorage is able to transmit both tensile and compressive as well as shearing and torsional forces from the rod to the screw.

This is accomplished by clamping action that is uniform peripherally (cf. FIGS. 2a-2c), i.e. around the entire cross-section, due to the fact that the contour of the rod cross-section nominally exactly coincides with the contour of the screw head opening and of the spacer in the area of contact, i.e. is congruent therewith. More specifically, the encircling clamping action is intended to act as a cage and to produce hydrostatic properties in the clamping plane, which can only be achieved with a cross-section having at least two plane-parallel surfaces.

Consequently, the invention relates to the rod cross-section with at least two plane-parallel sides, thereby allowing a uniform clamping action on the entire circumference, i.e. peripherally. Due to the uniform clamping action, maximal care is kept on the rod in the anchorage area, thereby allowing it to transmit the forces arising in the patient to the upper and lower pedicle screws safely and durably. Furthermore, the clamping action may be assisted by circumferential ridges in one or multiple planes. The clamping action is achieved either by an external or internal nut with a separate spacer or by an external or internal nut with an integrated spacer.

Another advantage of the plane-parallel cross-section is the variability of the stiffness in different directions. Thus, for example, the stiffness in the anterior/posterior direction can be increased in a dedicated manner with a minimum volume increase, which may be an essential advantage for patients suffering from vertebral slippage (spondylolisthesis).

Furthermore, the plane-parallel sides may most preferably be provided with a taper whose flanks each form an angle 37 of at least 10° with respect to the frontal plane of the rod in order to facilitate its introduction into pedicle screws that do not extend parallelly.

Figure 1:
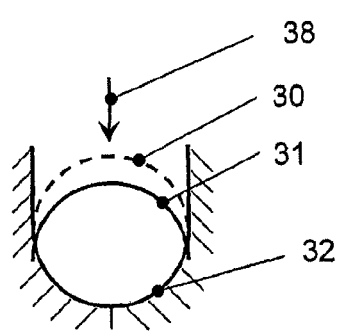
FIG. 1 A round rod between two semicircles (prior art).

FIG. 1 illustrates the conflict that arises when a circular rod 30 is clamped between two semicircles 31, 32. The semicircles 31, 32 would have to be able to interpenetrate. This would indeed be possible with complex comb-like tapering portions, but the plastic rod 30 would inevitably flow into the comb openings and be distorted.

Figure 2A:
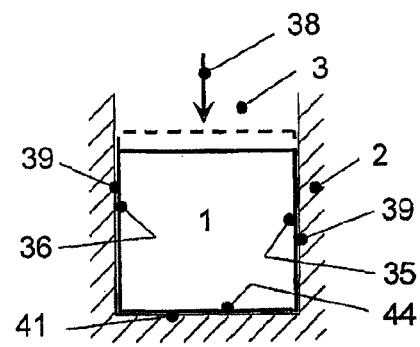
FIG. 2a An exemplary cross-section having 4 sides.

By way of example, FIG. 2a illustrates a cross-section having 4 sides of which at least two 35, 36 are plane-parallel. In this manner, a uniform peripheral fixation can be achieved by a clamping action (arrow 38, clamping device 4) parallel to the plane-parallel lateral surfaces. For this purpose, the distance between the sidewalls 39 of the opening 3 is closely fitted to the distance between the lateral faces 35, 36 of the rod 1 so that the rod is tightly held between the sidewalls 39 substantially without any lateral play. Complementarily, the bottom side 41 of the opening 3 is complementarily shaped to the lower side 44 of rod 1 so that the all sides of the rod 1 opposed to sides 39, 41 of the opening 3 tightly and play-free abut against these sides once the rod 1 is inserted into the opening 3.

Figure 2B:
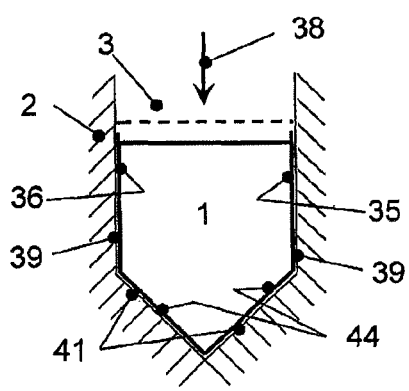
FIG. 2b An exemplary cross-section having 5 sides.

FIG. 2b illustrates a second exemplary cross-section having 5 sides with the same properties as that of FIG. 2a, in particular two parallel sides 35, 36.

Figure 2C:
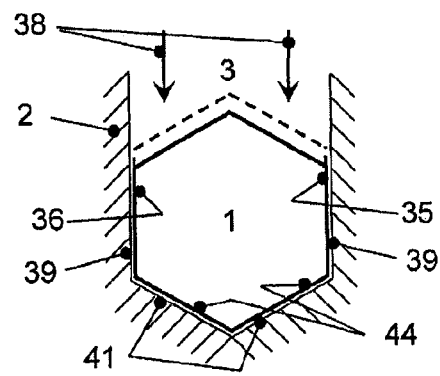
FIG. 2c An exemplary cross-section having 6 sides.

FIG. 2c illustrates a third exemplary cross-section having 6 sides with the same properties as that of FIG. 2a.

Figure 3A:
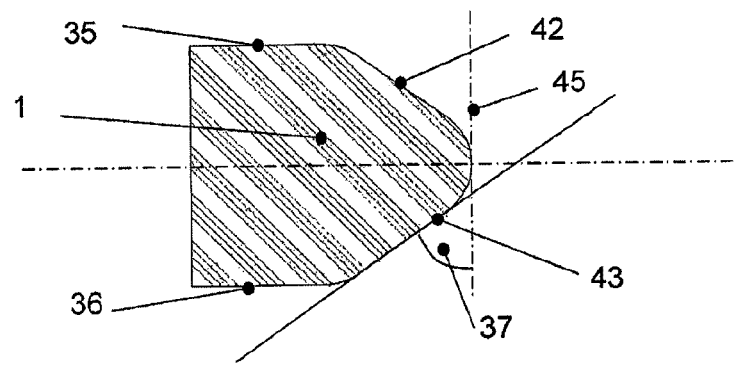
FIG. 3a A typical cross-section having 5 sides and a taper.

FIG. 3a illustrates an exemplary rod 1 having 5 sides of which 2 sides 35, 36 are plane-parallel and 2 tapering flanks 42, 43 are bevelled. The bevel angle 37 of the tapered flanks 42, 43 is at least 10° with respect to the frontal plane 45 of the rod on either side. Hence, the frontal plane 45 is a virtual plane orthogonal to the parallel sides 35, 36.

Figure 3B:
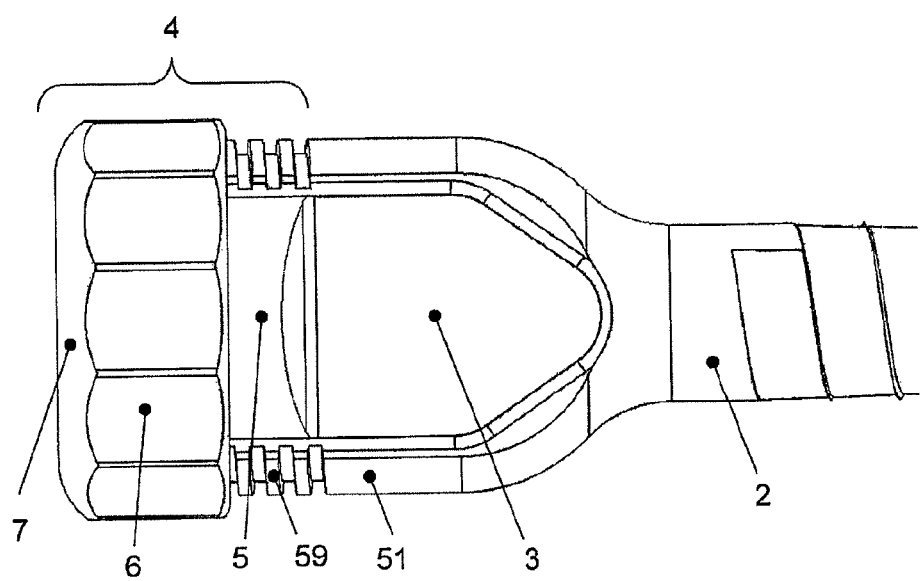
FIG. 3b The opening between the screw head and the spacer whose contour is congruent with the rod.

FIG. 3b illustrates a corresponding pedicle screw 2 with the opening contour 3 that is congruent with the rod 1 of FIG. 3, the screw head 51, the screw thread 59, the clamping device 4 including e.g. a spacer 5 and a clamping element 6.

FIG. 3c illustrates the rod 1, the screw 2, the spacer 5, and an external nut 7 as the clamping element 6. The nut 7 is screwed on a thread 59 with the nut 7 exteriorly surrounding the head 51 in the assembled situation in a sectional view.

Figures 4A, 4B:
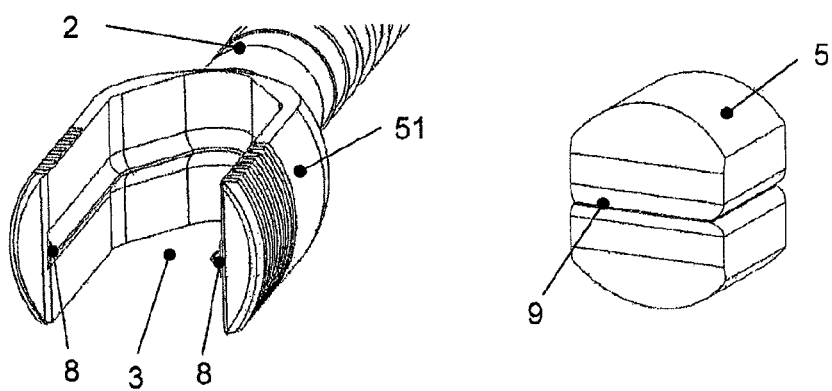
FIG. 4a The rod opening with a circumferential clamping ridge.
FIG. 4b A spacer with a clamping ridge.

FIG. 4a illustrates an opening 3 in the screw head 51 with a central ridge 8.

FIG. 4b illustrates the corresponding spacer 5 with side notches complementary to the ridge 8. The spacer 5 is provided with a ridge 9 which completes the ridge 8 to a circumferential ridge once the spacer 5 is inserted in the opening 3.

Figures 5A, 5B:
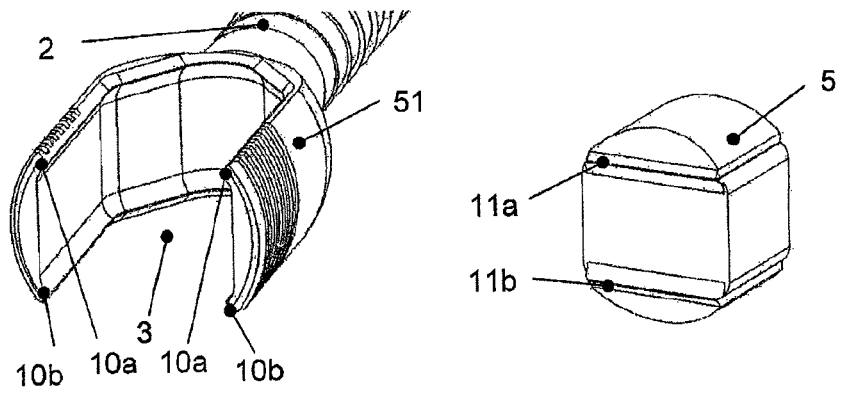
FIG. 5a The rod opening with two circumferential clamping ridges.
FIG. 5b A spacer with two clamping ridges.

FIG. 5a illustrates an opening 3 in the screw head 51 with an upper ridge 10a and a lower ridge 10b.

FIG. 5b illustrates the corresponding spacer 5 with upper side notches and lower side notches. The notches are complementarily shaped to the ridges 10. As noted above, this spacer 5 is provided with an upper ridge 11a and a lower ridge 11b complementing the ridges 10 a/b to a complete circumferential ridge.

In these variants, the circumferential ridge or ridges constitute the area of contact, the contour of which is substantially identical to the contour of the rod.

Figure 6:
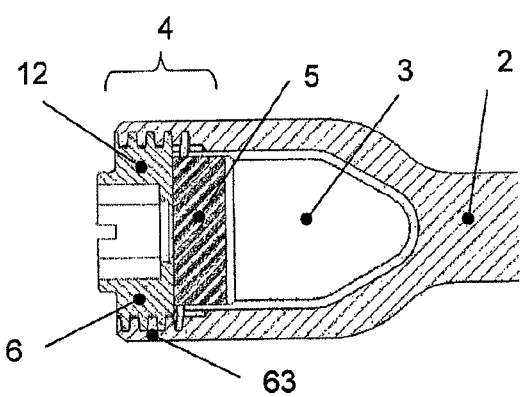
FIG. 6 A variant using an internal nut and a separate spacer.

FIG. 6 illustrates a variant using an internal nut 12 with a separate spacer 5 as the clamping device 4. Accordingly, the thread 63 for holding the clamping device 4 is machined inside the opening 3.

Figure 7:
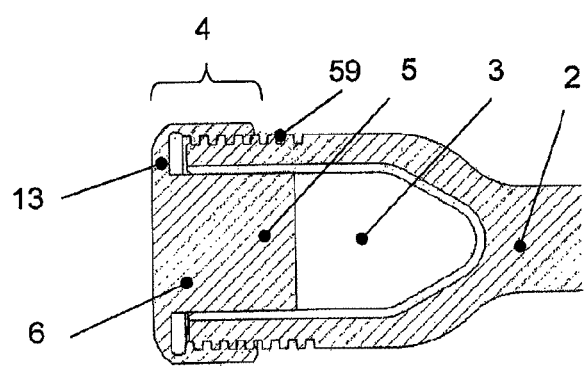
FIG. 7 A variant using an external nut and an integrated spacer.

FIG. 7 illustrates a variant using an external nut 13 with an integrated spacer 5 as the clamping device 4.

Figure 8:
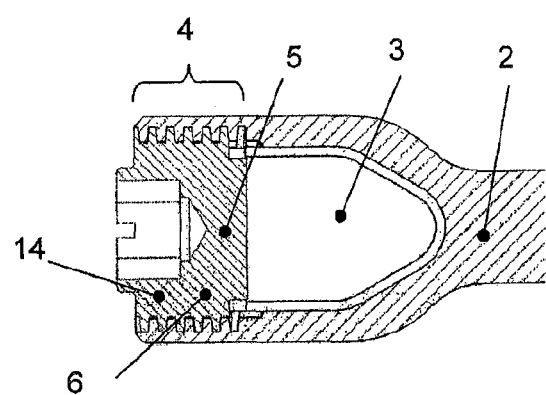
FIG. 8 A variant using an internal nut and an integrated spacer.

FIG. 8 illustrates a variant using an internal nut 14 with an integrated spacer 5 as the clamping device 4.

On the basis of the foregoing description, the one skilled in the art may conceive numerous variations of the invention without leaving the scope of protection which is defined by the claims. Such modifications may be:

The bevel angle of the beveled flanks is different.

The part between the beveled flanks may be rounded (cf. FIG. 3a), essentially constituted by an edge or more generally by a polygonal line, with or without part or all corners rounded.

The bevel angle is chosen in a range from 10° to 80°, and is preferably about 60°.

What is claimed is:

1. An anchorage arrangement for a connecting plastic rod for surgical treatment of a spine, the anchorage arrangement comprising:
    the connecting plastic rod including at least two plane-parallel surfaces; and
    a plurality of bone screws, each bone screw comprising a bottom side and sidewalls defining an opening, the opening positioned and configured to receive the connecting plastic rod;
    each bone screw comprising a ridge positioned in the opening;
    a clamping device comprising a clamping element and a spacer together positioned and configured to provide a clamping action in a direction parallel to the at least two plane-parallel surfaces so as to clamp an entire circumference of the rod; and
    the spacer comprising a spacer ridge;
    wherein a distance between the sidewalls is adapted to a distance of the plane-parallel surfaces in an area of contact so that the rod is snugly slidable in the opening,
    wherein, with the rod in the opening:
        the ridge and the spacer ridge together comprise a continuous circumferential ridge projecting toward the rod,
        the continuous circumferential ridge entirely surrounds the rod,
        the entire length of the continuous circumferential ridge is in contact with the rod, and
        a contour of the bottom side and the sidewalls defined by the ridge coincide substantially with a cross-section of the rod and together with the spacer ridge compress the rod to produce hydrostatic properties for the rod according to the clamping action.

2. The anchorage arrangement according to claim 1, wherein a bottom surface of the opening extending between the sidewalls and a corresponding front face of the rod are closely fitted to each other so that the rod is insertable in the opening in a configuration substantially free of play so as to constrain lateral movement.

3. The anchorage arrangement according to claim 1, wherein the plastic rod has at least 4 sides.

4. The anchorage arrangement according to claim 1, wherein the rod includes a front face comprising at least one effective bevel portion substantially delimited on an edge by a front edge of one surface of the at least two plane-parallel surfaces, the bevel positioned and configured to facilitate insertion of the rod into the opening, the bevel portion being beveled by an angle of at least 10° relative to a plane orthogonal to the plane-parallel surfaces.

5. The anchorage arrangement according to claim 4, wherein the bevel portions comprise an entire front face of the rod extending between the plane-parallel surfaces.

6. The anchorage arrangement according to claim 5, further comprising multiple circumferential ridges and complementary notches in different planes positioned and configured to assist the clamping of the entire circumference of the cross-section of the rod.

7. The anchorage arrangement according to claim 4, wherein the angle is at most 80°.

8. The anchorage arrangement according to claim 4, wherein the angle is 60°.

9. The anchorage arrangement according to claim 1, further comprising at least one circumferential ridge-notch arrangement positioned in the opening and configured to assist the clamping of the entire circumference of the cross-section of the rod.

10. The anchorage arrangement according to claim 1, wherein the spacer comprises a front face shaped complementary to a rear side of the rod on a region of the rod facing the clamping device, and the clamping element is configured to be fixated on a head of a bone screw.

11. The anchorage arrangement according to claim 10, wherein the clamping element is an external or internal nut, and the spacer is a part formed separately from the clamping element.

12. The anchorage arrangement according to claim 10, wherein the clamping device is a one-piece external nut or internal nut integrally formed spacer.

13. The anchorage arrangement according to claim 1, wherein the plastic rod is manufactured from polycarbonate urethane.

14. An anchorage arrangement according to claim 1, wherein the distance between the sidewalls is configured such that a contour of the rod at the at least two plane-parallel surfaces coincides with the contour of the bone screw at the sidewalls.

15. An anchorage arrangement according to claim 1, wherein the distance between the sidewalls is adapted to a distance of the plane-parallel surfaces in the area of contact such that the entire circumference of the rod remains without alteration due to flowing of a material of the rod due to the clamping action.

* * * * *